United States Patent [19]

Peck et al.

[11] Patent Number: 5,358,971
[45] Date of Patent: Oct. 25, 1994

[54] SUBSTITUTED 2-AMINOTETRALINS

[75] Inventors: James V. Peck; Gevork Minaskanian, both of Richmond, Va.

[73] Assignee: Whitby Research, Inc., Richmond, Va.

[21] Appl. No.: 131,845

[22] Filed: Oct. 4, 1993

Related U.S. Application Data

[60] Division of Ser. No. 837,229, Feb. 18, 1992, Pat. No. 5,274,003, which is a continuation-in-part of Ser. No. 375,583, Jul. 5, 1989, abandoned.

[51] Int. Cl.$^5$ .................. A61K 31/135; C07C 217/10
[52] U.S. Cl. ........................ 514/651; 564/347; 564/352; 564/353; 564/354; 549/304; 549/466
[58] Field of Search ............... 564/347, 352, 353, 354; 514/651

[56] References Cited

U.S. PATENT DOCUMENTS 5,070,106 12/1991 Casagrande .................. 514/651

OTHER PUBLICATIONS

McDermed et al "Synthesis and Pharmacology of Some 2-Aminotetralins" J. Med Chem. 18 362–367 (1975).

*Primary Examiner*—Celia Chang
*Attorney, Agent, or Firm*—Richard J. Hammond

[57] ABSTRACT

Optically active or racemic compounds are provided having the formula

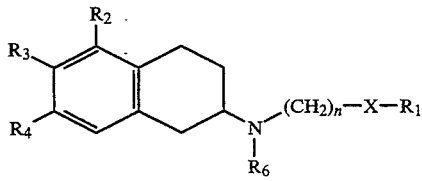

where $R_2$, $R_3$ and $R_4$ are selected from the group consisting of H and OA with the provision that at least one of $R_2$, $R_3$ and $R_4$ is H, that $R_2$ and $R_4$ are not both OA; A is H or is selected from the group consisting of hydrocarbyl radicals, said hydrocarbyl radicals being further optionally substituted with radicals selected from the group consisting of

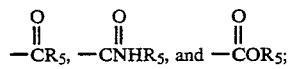

$R_5$ is selected from the group consisting of alkyl and aromatic residues, preferably radicals having between 1 and 12 carbon atoms, including alkyl, alkyl substituted with aryl radicals, and aryl radicals substituted with alkyl radicals; n is an integer between 1 and 4; $R_6$ is an alkyl chain comprising between 1 and 4 carbon atoms; X is oxygen; and $R_1$ is selected from the group consisting of

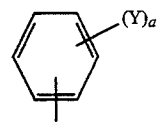

wherein Y is as defined in the specification, and a is an integer of from zero to 3.

These compounds are useful in treatment of disorders of the central nervous, cardiovascular, and endocrine systems, such as for inducing anorexia and weight loss in humans.

14 Claims, No Drawings

SUBSTITUTED 2-AMINOTETRALINS

This application is a division of application Ser. No. 07/837,229, filed Feb. 18, 1992, now U.S. Pat. No. 5,274,003, which is a continuation-in-part of application Ser. No. 07/375,583, filed Jul. 5, 1989 now abandoned.

BACKGROUND OF THE INVENTION

1. Field of the Invention

The invention relates generally to substituted 2-aminotetralins and to processes for preparing such compounds. More particularly, the invention relates to compounds for therapeutic use, in particular, in treating disorders of the central nervous, cardiovascular and endocrine systems. The compounds of this invention are also useful for alleviating glaucoma, Parkinsonism and schizophrenia, and for inducing anorexia and weight loss in mammals.

2. Background of the Prior Art

It is known that various hydroxylated 2-aminotetralins of the general formula

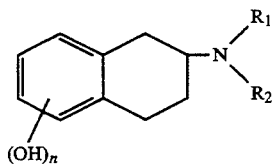

where $R_1$ and $R_2$ are saturated alkyl groups and n is 1 or 2, are dopamine receptor agonists (McDermed et al., *J. Med. Chem.*, 18, 362 (1975); Feenstra et al., *Arch. Pharmacol.*, 313, 213 (1980)).

Many structure-activity relationship studies have been conducted to find compounds with high dopamine-receptor stimulating activity. A survey is contained in Katerinopoulos, H. E., et al., "Structure-Activity Relationships for Dopamine Analogues", *Drugs of the Future*, Vol. 12, No. 3, 1987, 223–253. Based upon the high activity of apomorphine, many derivatives and simplified structural analogues have been tested and found to have dopaminergic activity. For instance, some of the bicyclic analogues of dopamine, 2-amino-5,6- and 2-amino-6,7-dihydroxytetralin, and their N-alkylated derivatives were tested and showed activity.

In addition, studies have shown that the 5-hydroxy derivatives of 2-aminotetralins possess high potency almost equivalent to that of the 5,6 catechols, with the additional advantage of increased stability, selectivity and duration of biochemical action. These studies have also shown that in bicyclic compounds the size of the two nitrogen substituents controls activity. For instance, the N-butyl and N,N-dibutyl derivatives of 2-amino-5,6-dihydroxytetralin, dopamine and norapomorphine have little or no dopaminergic activity, while analogues having at least one N-ethyl or N-n-propyl group posses high activity.

Further studies have shown that the $D_2$ receptor potency of dopamine agonists is at a maximum when one of the two N-substituents fits into a receptor niche which, because of size constraints, maximally accommodates an n-propyl group. Conversely, activity drops off when the propyl group is replaced by the smaller groups ethyl or methyl. When the compound contains no N-substituent at least as small as n-propyl, activity is small or non-existent.

However, the structural requirements for the second N-substituent in such compounds have not been established. Consequently, the search continues for new and better N-substituents to enhance both dopamine receptor binding and activity, especially as shown by in vivo studies designed to test the dopaminergic activity of compounds, such as contralateral turning studies in 6-OH-DA-lesioned rats. See Seiler, Max P., et al., "Structure-Activity Relationships of Dopaminergic 5-Hydroxy-2-aminotetralin Derivatives with Functionalized N-Alkyl Substituents", *J. Med. Chem.*, 1986, 29, 912–917.

The receptor site into which this second N-substituent is thought to interact appears to accommodate a wide variety of large, bulky groups having different functionalities without loss of activity. See McDermed, J. D., et al., *J. Med. Chem.*, 1975, 18, 362; Cannon, J. G., et al., *J. Med. Chem.*, 1977, 20, 1111; and Wikstroem, H., et al., *J. Med. Chem.*, 1982, 25, 925. However, the dopaminergic activity and potency conferred upon the compound by the choice of the second N-substituent is, at present, unpredictable so that the search continues for new and better dopamine receptor agonists, especially for compounds showing a high degree of selectivity and specificity as either $D_1$ or $D_2$ receptor agonists.

SUMMARY OF THE INVENTION

There has now been discovered certain novel compounds having dopaminergic activity and having the structural formula

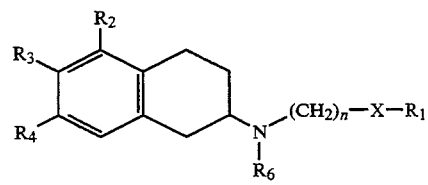

where $R_2$, $R_3$ and $R_4$ are each selected from the group consisting of H and OA with the provision that at least one of $R_2$, $R_3$ and $R_4$ is H, that $R_2$ and $R_4$ are not both OA; A is H or is selected from the group consisting of hydrocarbyl radicals, for example lower alkyl radicals optionally substituted with aliphatic residues (i.e., methyl, ethyl, propyl, benzyl, etc.), as well as

$R_5$ is selected from the group consisting of alkyl and aromatic residues having between 1 and 12, preferably between 1 and 6, carbon atoms, for example, alkyl optionally substituted with aromatic residues and aromatic residues optionally substituted with alkyl radicals; n is an integer between 1 and 4; $R_6$ is an alkyl chain comprising between 1 and 4 carbon atoms; X is selected from the group consisting of —$CH_2$—, oxygen, sulfur, and nitrogen, with the provision that when X is not —$CH_2$—, $R_1$ is selected from the group consisting of

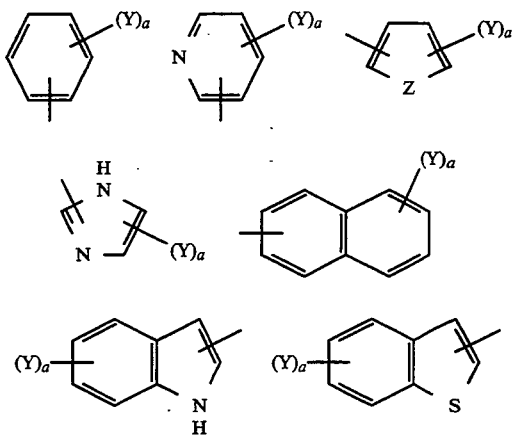

wherein Z is oxygen, nitrogen or sulfur; and Y is selected from the group consisting of hydroxy, nitro, cyano, azido, amino, acylamino, carboxyamido, trifluoromethyl, sulfate, sulfonamido, halogen, hydrocarbyl, and heteroatom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3; and with the further provision that when X is —$CH_2$—, $R_1$ is either

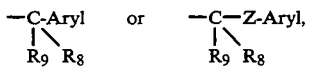

wherein $R_8$ is hydrogen, aryl, or $R_6$; and further wherein $R_9$ is aryl, $R_6$, —OH, —$NH_2$,

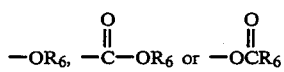

or —N $(R_6)_2$; or $R_1$ is

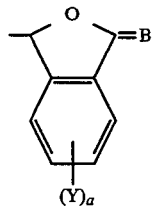

wherein B is oxygen, sulfur or two hydrogen atoms, and pharmaceutically acceptable salts thereof.

Preferably, $R_2$ is OA and A is H.

It is essential that the compounds in the present invention be an optically active compound or racemic mixtures thereof having substantial affinity and selectivity for binding to dopamine $D_2$ receptors, e.g., in a human. In particular, it is found that 2-(N-n-propyl, N-2-[phenyloxy]ethylamino)-5-hydroxytetralin is especially preferred for its high affinity and selectivity for binding to dopamine $D_2$ receptors.

DETAILED DESCRIPTION OF THE INVENTION

The compounds used in the present invention are selected from the group of stereoisomers or racemic mixtures thereof of compounds having dopaminergic activity represented by the formula:

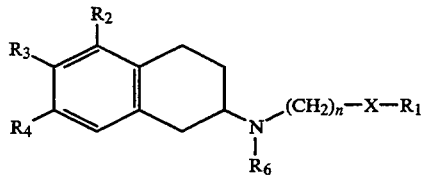

wherein $R_2$, $R_3$ and $R_4$ are each selected from the group consisting of H and OA with the provision that at least one of $R_2$, $R_3$ and $R_4$ is H, that $R_2$ and $R_4$ are not both OA; A is H or is selected from the group consisting of hydrocarbyl radicals, for example, lower alkyl radicals, optionally substituted with

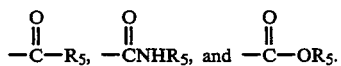

$R_5$ is selected from the group consisting of alkyl and aromatic residues having between 1 and 12, preferably between 1 and 6, carbon atoms, for example, alkyl residues optionally substituted with aromatic residues and aromatic residues optionally substituted with alkyl radicals; n is an integer between 1 or 4; $R_6$ is an alkyl chain comprising between 1 and 4 carbon atoms; X is selected from the group consisting of —$CH_2$—, oxygen, sulfur, and nitrogen, with the provision that when X is not —$CH_2$—, $R_1$ is selected from the group consisting of

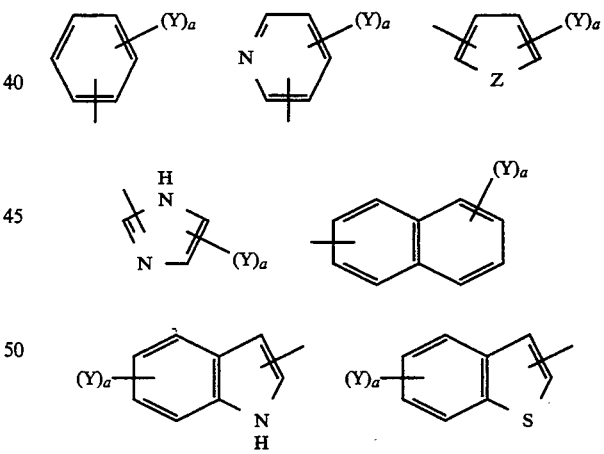

wherein Z is oxygen, nitrogen or sulfur; and Y is selected from the group consisting of hydroxy, nitro, cyano, azido, amino, acylamino, carboxyamido, trifluoromethyl, sulfate, sulfonamido, halogen, hydrocarbyl and heteroatom-substituted hydrocarbyl radicals, wherein said heteroatoms are selected from the group consisting of halogen, nitrogen, oxygen, sulfur and phosphorus and said hydrocarbyl radicals comprise from 1 to 12, preferably 1 to 6, carbon atoms, and a is an integer of from zero to 3, for instance, zero to 2; and with the further provision that when X is —$CH_2$—, $R_1$ is either

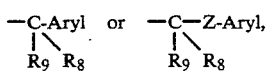

wherein $R_8$ is hydrogen, aryl, or $R_6$; and further wherein $R_9$ is aryl, $R_6$, —OH,

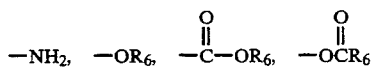

or —N($R_6$)$_2$; or $R_1$ is

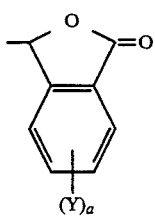

wherein B is oxygen, sulfur or two hydrogen atoms, and pharmaceutically acceptable salts thereof.

Preferably, $R_2$ is OA and A is H.

A is preferably H or is selected from the group consisting of phenyl and alkyl radicals having from 1 to 12 carbon atoms. More preferably, $R_5$ is an alkyl or aryl radical that would serve to extend the activity of the compound in the body, for example, phenyl, methyl, t-butyl, o-methylphenyl, o-, m- or p-methoxyphenyl, p-isopropylphenyl or nonyl.

The more preferred groups represented by $R_1$ are thienyl, phenyl, hydroxyphenyl, furanyl and naphthalenyl, e.g., 2-thienyl, 3-thienyl, 3-hydroxyphenyl, 4-hydroxyphenyl, etc.

In the more preferred compounds for use in the present invention, n is 2, X is oxygen or —CH$_2$—, and $R_2$ is OA; and most preferably, A is H and $R_6$ is propyl.

It is essential that the compounds herein be an optically active or racemic mixtures capable of binding selectively to one or more dopamine D$_2$ receptors, e.g., in a human. In particular, 2-(N-n-propyl,N-2-[phenyloxy]ethylamino)-5-hydroxytetralin is an especially preferred compound because of its high affinity and selectivity for binding to D$_2$ dopamine receptors. Due to their high affinity for binding to D$_2$ dopamine receptors, the compounds herein will be useful in the treatment of disorders of the central nervous, cardiovascular, and endocrine systems. In particular, the compounds herein are useful in the treatment of such conditions in humans as elevated intraocular pressure, schizophrenia and Parkinsonism, and for inducing anorexia and weight loss in humans and other mammals.

Particularly preferred compounds are as follows:

Compounds wherein X is oxygen, nitrogen or sulfur and $R_1$ is selected from the group consisting of radicals represented by the general formula

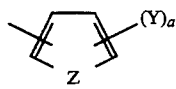

wherein specific preferred compounds of this group include:

2-(N-n-propyl-N-2-[2-thienyloxy]ethylamino)-5-hydroxytetralin;
2-(N-n-propyl-N-2-[3-thienyloxy]ethylamino)-5-hydroxytetralin;
2-(N-n-propyl-N-2-[2-furanyloxy]ethylamino)-5-hydroxytetralin;
2-(N-n-propyl-N-2-[3-furanyloxy]ethylamino)-5-hydroxytetralin;
2-(N-n-propyl-N-2-[2-(4-methyl)thienyloxy]ethylamino-5-hydroxytetralin;
2-(N-n-propyl-N-2-[2-(3,4,5-trimethyl)thienyloxy]ethylamino)-5-hydroxytetralin;
2-(N-n-propyl-N-2-[2-(5-chloro)thineyloxy]ethylamino)-5-hydroxytetralin;
2-(N-n-propyl-N-2-[2-(4-bromo-5-methyl)thienyloxy]ethylamino)-5-hydroxytetralin;
2-(N-n-propyl-N-2-[2-(4-methyl-5-ethyl)thienyloxy]ethylamino)-5-hydroxytetralin.

Compounds wherein X is oxygen, nitrogen or sulfur and wherein $R_1$ is selected from the group of radicals represented by the formulae

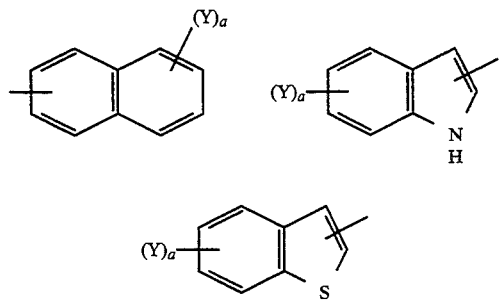

More preferably, in these compounds Y comprises no more than 5 carbon atoms and a is an integer from zero to 2. Specific preferred compounds of this group include:

2-(N-n-propyl-N-2-[2-naphthalenyloxy]ethylamino)-5-hydroxytetralin;
2-(N-n-propyl-N-2-[4-indolyloxy]ethylamino)-5-hydroxytetralin;
2-(N-n-propyl-N-2-[2-benzothienyloxy]ethylamino)-5-hydroxytetralin; and
2-(N-n-propyl-N-2-[3-benzothienyloxy]ethylamino)-5-hydroxytetralin.

Compounds wherein $R_1$ is phenyl and/or substituted phenyl and is selected from the group of radicals represented by the formula

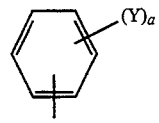

and wherein X is oxygen, nitrogen or sulfur. Specifically preferred compounds of this group include:

2-(N-n-propyl-N-2-[phenyloxy]ethylamino)-5-hydroxytetralin;
2-(N-n-propyl-N-2-[4-hydroxyphenyloxy]ethylamino)-5-hydroxytetralin;
2-(N-n-propyl-N-2-[3-hydroxyphenyloxy]ethylamino)-5-hydroxytetralin;
2-(N-n-propyl-N-2-[phenyloxy]ethylamino)-5-methoxytetralin;

2-(N-n-propyl-N-2-[phenylamino]ethylamino)-5-hydroxytetralin;

2-(N-n-propyl-N-2-[4-hydroxyphenylamino]ethylamino)-5-hydroxytetralin;

2-(N-n-propyl-N-3-[phenyloxy]propylamino)-5-hydroxytetralin;

2-(N-n-propyl-N-2-[2,6-dimethylphenyloxy]ethylamino-5-hydroxytetralin; and 2-(N-n-propyl-N-2-[3,5-dimethylphenyloxy]ethylamino-5-hydroxytetralin.

Compounds wherein X is —CH$_2$— and R$_1$ is selected from the group consisting of radicals represented by the formulae:

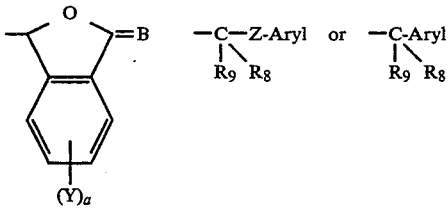

and wherein B is O, S, or H$_2$. Specific preferred compounds in this group include:

3-[2-[propyl(1,2,3,4-tetrahydro-5-methoxy-2-naphthalenyl)amino]ethyl]-l(3H)-isobenzofuranone;

3-[2-[propyl(1,2,3,4-tetrahydro-5-hydroxy-2-naphthalenyl)amino]ethyl]-l(3H)-isobenzofuranone;

6-[[2-(1,3-dihydro-1-isobenzofuranyl)ethyl]propylamino]5,6,7,8-tetrahydro-1-naphthalenol;

2-(N-n-propyl-N-3,3,3-triphenylpropylamino)-5-hydroxytetralin;

2-(N-n-propyl-N-2,2,2-triphenylethylamino)-5 -hydroxytetralin;

2-(N-n-propyl-N-3,3-diphenylpropylamino)-5-hydroxytetralin;

2-(N-n-propyl-N-2,2-diphenylethylamino)-5-hydroxytetralin;

2-(N-n-propyl-N-2-phenylpropylamino)-5-hydroxytetralin;

2-(N-n-propyl-N-2-phenylpropylamino)-5-methoxytetralin;

2-(N-n-propyl-N-2-(2-methoxy)phenethylamino)-5-hydroxytetralin;

2-[N-n-propyl-N-2-(2-phenyloxy)propylamino]-5-hydroxytetralin;

6-[[2-(1,3-dihydro-1-isobenzofuranyl)ethyl]propylamino]-5,6,7,8-tetrahydro-1-naphthalenol;

(S,R)-3-[2-[propyl(1,2,3,4-tetrahydro-5-hydroxy-2-naphthalenyl)amino]ethyl]-l(3H)-isobenzofuranone;

(S,S)-3-[2-[propyl(1,2,3,4-tetrahydro-5-hydroxy-2-naphthalenyl)amino]ethyl]-l(3H)-isobenzofuranone.

EXAMPLES

The invention is further illustrated by the following examples which are illustrative of various aspects of the invention, and are not intended as limiting the scope of the inventions defined by the appended claims.

EXAMPLE 1

Preparation of 2-[N-n-propyl,N-2-(phenyloxy)ethylamino]-5-methoxytetralin.

A mixture of 2-(N-n-propylamino)-5-methoxytetralin (7.0 g, 0.0319 mol; prepared according to *J. Chem. Soc.*, 1965, pp. 26–36), phenoxyacetic acid (4.86 g, 0.0319 mol), and borane trimethylamine complex (2.33 g, 0.0319 mol) was refluxed in xylenes overnight. The cooled reaction mixture was extracted with NaHCO$_3$ and the organic layer was dried over MgSO$_4$, filtered and concentrated under reduced pressure. The resulting oil was subjected to flash chromatography (silica; 9:1 pet ether/EtOAc) and product was isolated: NMR of the free base (300 MHz, CDCl$_3$): δ7.3–6.6(m, 8H), 4.0(t, 2H), 3.7(s, 3H), 3.1–2.5(m, 9H), 2.1(m, 1H), 1.7–1.4(m, 3H), 0.9(t, 3H). The free base thus isolated was converted to a hydrochloride salt by the addition of dry ether-HCL.

EXAMPLE 2

Preparation of 2-[N-n-propyl,N-2-(phenyloxy)ethylamino]-5-hydroxytetralin.

A mixture of pyridine hydrochloride and the product of Example 1 was heated in an oil bath at 200° C. When the reaction was complete (TLC), it was cooled, diluted with H$_2$O, made basic with NH$_4$OH and extracted with ether. The organic layer was dried over MgSO$_4$, filtered and concentrated under reduced pressure. The residue was subjected to flash chromatography (Silica: 8:2 pet ether/EtOAc). The product was dissolved in ether and converted to a hydrochloride salt by the addition of dry ether- HCl. Anal. Calcd. for C$_{21}$H$_{27}$NO$_2$. HCl: C, 69.69; H, 7.80; N, 3.87. Found: C, 69.54; H, 7.90; N, 3.87. NMR of the free base (300 MHz, CDCl$_3$): δ7.3–6.6(m, 8H), 4.0(t, 2H), 3.1–2.5(m, 9H), 2.1(m, 1H), 1.7–1.4(m, 3H), 0.9(t, 3H).

EXAMPLE 3

The product of Example 2 was also obtained by dissolving the product of Example 1 in dry dichloromethane and adding a solution of boron tribromide in dichloromethane dropwise at room temperature under nitrogen. After completion, the reaction was poured into a beaker containing NH$_4$OH and ice and stirred for 0.5 h. The organic layer was separated, and the product was purified as in Example 2.

EXAMPLE 4

Preparation of 2-[N-n-propyl,N-3-(phenyloxy)propylamino]-5-methoxytetralin.

In Example 1, phenoxyacetic acid can be replaced by 3-phenoxypropionic acid.

EXAMPLE 5

Preparation of 2-[N-n-propyl,N-3-(phenyloxy)propylamino]-5-hydroxytetralin.

The product of Example 4 can be used as the starting material for Example 2.

EXAMPLE 6

Preparation of 2-[N-n-propyl,N-2-(1-naphthalenyloxy)-ethylamino]-5-methoxytetralin.

In Example 1, phenoxyacetic acid was replaced by (1-naphthoxy)-acetic acid. The resulting oil was subjected to flash chromatograph (silica; pet ether) and the product was isolated; characteristic peak of NMR (300 MHz, CDCl$_3$); δ8.3–6.7 (m, 10H), 4.2(m, 2H), 3.85(s, 3H), 1.0(t, 3H).

EXAMPLE 7

Preparation of 2-[N-n-propyl,N-3-(1-naphthaienyloxy)-propylamino]-5-hydroxytetralin.

The product of Example 6 was used as the starting material in Example 2. The resulting oil was subjected to flash chromatography and the isolated product showed characteristic peaks at: NMR(CDCl$_3$) δ8.3–6.6(m, 10H), 4.2(m, 2H), 0.9(t 3H).

EXAMPLE 8

Preparation of 3-[2-[propyl (1,2,3,4-tetrahydro-5-methoxy-2-naphthalenyl) amino]ethyl ]-1 (3H)-isobenzofuranone.

In Example 1, phenoxyacetic acid was replaced by phthalide-3-acetic acid. The resulting oil was subjected to flash chromatography and the isolated product showed distinct peaks at: NMR(CDCl$_3$) δ8.0–6.7(m, 7H), 5.7(m, 1H), 3.8(s, 3H), 0.9(t, 3H). Anal. Calc. for C$_{24}$H$_{29}$NO$_3$ . HCl: C, 69.30; H, 7.27; N, 3.37. Found: C, 69.08; H, 7.23; N, 3.28.

EXAMPLE 9

Preparation of 3-[2-[propyl(1,2,3,4-tetrahydro-5-hydroxy-2-naphthalenyl)amino]ethyl]-1(3H)-isobenzofuranone.

The product of Example 8 was used as the starting material for Example 3. The resulting oil after purification showed distinct peaks at: NMR(CDCl$_3$) δ7.9–6.6(m, 7H), 5.7(m, 1HO, 0.95(t, 3H). Anal. Calc. for C$_{23}$H$_{27}$NO$_3$ . HCl: C, 68.73; H, 7.02; N, 3.48. Found: C, 68.62; H, 7.09; N, 3.35.

EXAMPLE 10

Preparation of 6-[[2-(1,3-dihydro-1-isobenzofuranyl)-ethyl]propylamino]-5,6,7,8-tetrahydro-1-naphthalenol.

The reduction of the product of Example 9 will result in the desired product.

EXAMPLE 11

Preparation of 2-[N-n-propyl,N-2,2-diphenylethylamino)-5-methoxytetralin.

In Example 1, phenoxyacetic acid was replaced by diphenylacetic acid. The purified product showed characteristic peaks at: NMR(CDCl$_3$) δ7.8–6.65(m, 13H), 4.1(t, 1HO, 3.8(s, 3H), 3.2 ( d, 2H) , 0.7 ( t, 3H) .

EXAMPLE 12

Preparation of 2-[N-n-propyl,N-2,2-diphenylethylamino]-5-hydroxytetralin.

The product of Example 11 was used as starting material in Example 3. After purification, the product showed distinct peaks at: NMR(CDCl$_3$) δ7.8–6.65(m, 13H) , 4.1(t, 1H) , 3 2 (d, 2H) 0.7(t, 3H). Anal. calc. for C$_{27}$H$_{31}$NO . HCl: C,76.84; H, 7.64; N, 3.32. Observed: C, 77.00; H, 7.69; N, 3.21.

EXAMPLE 13

Preparation of 2-[N-n-propyl,N-3,3-diphenylpropylamino]-5-methoxytetralin.

In Example 1, phenoxyacetic acid was replaced by 3,3-diphenylpropionic acid. The purified product showed distinct peaks at: NMR (CDCl$_3$ ) δ7.4–7.2(m, 11H), 6.65(m, 2H), 4.05(t, 1H), 3.8(s, 3H), 0.9(s, 3H).

EXAMPLE 14

Preparation of 2-[N-n-propyl,N-3,3-diphenyipropylamino]-5-hydroxytetralin.

The product of Example 13 was used as starting material for Example 3. The isolated product showed distinct peaks at: NMR(CDCl$_3$) δ7.4–7.0(m, 1H), 6.7–6.5(m, 2H), 4.0(t, 1H), 0.9(t, 3H).

EXAMPLE 15

Preparation of 2-[N-n-propyl,N-2-(2-phenyloxy)-propylamino]-5-methoxytetralin.

In Example 1, phenoxyacetic acid was replaced by DL-2-phenoxypropionic acid. The purified product showed distinct peaks at: NMR(CDCl$_3$) δ7.3–6.65(m, 8H), 4.45(m, 1H), 3.8(s, 3H) , 0.9 (t, 3H) .

EXAMPLE 16

Preparation of 2- [N-n-propyl, N-2- (2-phenyloxy) propylamino]-5 -hydroxytetralin.

The product of Example 15 was used as starting material for Example 2. The isolated product showed characteristic peaks at: NMR(CDCl$_3$) δ7.3–6.65(m, 8H), 4.45(m, 1H), 0.9(t 3H).

EXAMPLE 17

Preparation of 2-[N-n-propyl,N-3,3,3-triphenylpropylamino]-5-methoxytetralin.

In Example 1, phenoxyacetic acid was replaced by 3,3,3-triphenylpropionic acid. The purified product showed characteristic peaks at: NMR(CDCl$_3$) δ7.4–6.65(m, 18H) , 3.8(s, 3H) , 0.9 ( t, 3H) .

EXAMPLE 18

Preparation of 2-[N-n-propyl,N-3,3,3-triphenylpropylamino]-5-hydroxytetralin.

The product of Example 17 was used as starting material in Example 3. After purification the product showed distinct peaks at: NMR(CDCl$_3$) δ7.4–6.65(m, 18H), 0.9(t, 3H).

EXAMPLE 19

Preparation of 2-[N-n-propyl,N-2,2,2-triphenylethylamino]-5-methoxytetralin.

In Example 1, phenoxyacetic acid can be replaced by triphenylacetic acid.

EXAMPLE 20

Preparation of 2-[N-n-propyl,N-2,2,2-triphenylethylamino]-5-hydroxytetralin.

The product of Example 19 can be used as the starting material for Example 3.

EXAMPLE 21

Preparation of 2-[N-n-propyl,N-2-[2-methoxy]phenethylamino]-5-methoxytetralin.

In Example 1, phenoxyacetic acid can be replaced by α-methoxyphenylacetic acid.

EXAMPLE 22

Preparation of 2-[N-n-propyl,N-2-(2-methoxy)-phenethylamino]-5-hydroxytetralin.

The product of Example 21 can be used as the starting material for Example 2.

EXAMPLE 23

Preparation of 2-[N-n-propyl,N-(2,3-dihydro-1H-inden-1-yl)methylamino]-5-methoxytetralin.

In Example 1, phenoxyacetic acid can be replaced by 1-indancarboxylic acid.

EXAMPLE 24

Preparation of 2-[N-n-propyl,N-(2,3-dihydro-1H-inden-1-yl)methylamino]-5-hydroxytetralin.

The product of Example 23 can be used as the starting material for Example 3.

EXAMPLE 25

Preparation of 2-[N-n-propyl,N-(tetrahydro-2-naphthyl)-methylamino]-5-methoxytetralin.

In Example 1, phenoxyacetic acid can be replaced by 1,2,3,4-tetrahydro-2-naphthoic acid.

EXAMPLE 26

Preparation of 2-[N-n-propyl,N-(tetrahydro-2-naphthyl)-methylamino]-5-hydroxytetralin.

The product of Example 25 can be used as the starting material for Example 3.

EXAMPLE 27

Preparation of 2-[N-n-propyl, N-2-(3,5-dimethylphenyloxy)ethylamino]-5-methoxytetralin.

In Example 1, phenoxyacetic acid can be replaced by 3,5-dimethylphenoxyacetic acid.

EXAMPLE 28

Preparation of 2-[N-n-propyl,N-2-(e,5-dimethylphenyloxy)ethylamino]-5-hydroxytetralin.

The product of Example 27 can be used as the starting material for Example 3.

EXAMPLE 29

Preparation of (−)-1,2,3,4-tetrahydro-5-methoxy-N-(2-phenoxyethyl)-N-propyl-2-naphthalenamine.

A mixture of (−)-2-(N-n-propylamino)-5-methoxytetralin (80 mg, 31.9 mmol; prepared according to $J.$ $Chem.$ $Soc.$, 1965, pp 26–36), phenoxyacetic acid (166 mg, 109.4 mmol) and borane trimethylamine complex (80 mg, 109.4 mmol) was refluxed in xylenes overnight. The cooled reaction mixture was extracted with NaHCO$_3$ and the organic layer was dried over MgSo$_4$, filtered and concentrated. The resulting oil was subjected to flash chromatography (Silica: 9:1 pet ether/EtOAc) and product was isolated with characteristic peaks at: NMR (300 MHz, CDCl$_3$); $\delta$7.3–6.6 (m, 8H), 4.0(t,2H), 3.7(S,3H), 3.1–2.5(m,9H), 2.1(m, 1H), 1.7–1.4 (m, 3H) 0.9 ( t, 3H) .

EXAMPLE 30

Preparation of (−)-5,6,7,8-tetrahydro-6-[(2-phenoxyethyl) propylamino]-1-naphthalenol.

To a mixture of 1.0M Boron tribromide in dichloromethane in 20 ML chloroform was added dropwise the product of Example 1 (80 mg, 0.236 mmol) in chloroform and stirred at room temperature of 15 min. After workup, the crude mixture was subjected to flash chromatography (Silica: 8.2 pet ether/EtOAc). The product showed characteristic peaks at: NMR (300 MHz, CDCl$_3$) $\delta$7.3–6.6(m, 8H), 4.0(t, 2H), 3.1–2.5(m,9H), 2.1(m, 1H), 1.7–1.4 (m, 3H), 0.9(t, 3H).

EXAMPLE 31

Preparation of 1,2,3,4-tetrahydro-5-methoxy-N-[2-(2naphthalenyloxy)ethyl]-N-propyl-2-naphthalenamine.

In Example 29, phenoxyacetic acid was replaced with (2-naphthoxy)acetic acid and (−)-2-(N-n-propylamino)-5-methoxy-tetralin was replaced with (±)-2-(N-n-propylamino)-5-methoxytetralin. The resulting oil was subjected to flash chromatography (Silica: 8:2 pet ether/EtOAc) and the product showed characteristic peaks at: NMR (300 MHz, CDCl$_3$) $\delta$7.8–6.6(m, 10H), 4.15(t, 2H), 3.8(S, 3H), 0.9(t, 3H).

EXAMPLE 32

Preparation of 5,6,7,8-tetrahydro-6-[(2-(2-naphthalenyloxy)ethyl]propylamino]-1-naphthalenol.

The product of Example 31 was used as the starting material in Example 30. The resulting crude was subjected to flash chromatography (Silica: 8:2 pet ether/EtOAc) and the product showed characteristic peaks at: NMR (300 MHz, CDCl$_3$) $\delta$7.8–6.55(m, 10H), 4.15(t, 2H), 0.9(t, 3H).

EXAMPLE 33

Preparation of 1,2,3,4-tetrahydro-5-methoxy-(2-thiophenoxyethyl)-N-propyl-2-naphthalenamine.

In Example 31, (2-naphthoxy)acetic acid was replaced with thiophenoxyacetic acid. The resulting oil was subjected to flash chromatography (Silica: 95:5 pet ether/EtOAc) and the product showed characteristic peaks at: NMR (300 MHz, CDCl$_3$) $\delta$7.4–7.0(m,6H), 6.65(M, 2H), 3.8(S, 3H), 0.9(t, 3H).

EXAMPLE 34

Preparation of 5,6,7,8-tetrahydro-6-[(2-thiophenoxyethyl)propylamino]-1-naphthalenol.

The product of Example 33 was used as the starting material in Example 30. The resulting crude was subjected to flash chromatography (Silica: 9:1 pet ether/EtOAc) and the product was isolated and showed characteristic peaks at: NMR (300 MHz, CDCl$_3$) $\delta$7.4–6.95 (m,6H), 6.6(m,2H), 0.9 (t,3H).

EXAMPLE 35

Preparation of (−)-3-[2-[propyl(1,2,3,4-tetrahydro-5-methoxy-2-naphthalenyl)amino]ethyl]-l(3H)-isobenzofuranone.

In Example 29, phenoxyacetic acid was replaced by phthalide-3-acetic acid. The resulting oil was subjected to flash chromatography (Silica: 7:3 pet ether/EtOAc) and the product showed characteristic peaks at: NMR (300 MHz, CDCl$_3$) $\delta$7.9–6.6(m, 7H), 5.7(dd, 1H),3.8(S, 3H), 0.9(t, 3H).

EXAMPLE 36

Preparation of (S,R)-3-[2-[propyl(1,2,3,4-tetrahydro-5-hydroxy-2-naphthalenyl)amino]ethyl]-l(3H)-isobenzofuranone.

The product of Example 35 and excess pyridine hydrochloride were heated in an oil bath at 200° C. for 1 hr. The reaction was cooled, diluted with H$_2$O, basified with NH$_4$OH and extracted with ether. The organic layer was dried over MgSO$_4$, filtered, and concentrated under reduced pressure. The residue was subjected to flash chromatography (Silica: 6:4 pet ether/EtOAc) and the product [upper isomer by TLC (Silica: 1:1 pet ether/EtOAc) showed characteristic peaks at: NMR (300 MHz, CDCl$_3$) $\delta$7.9–6.6(m, 7H), 5.7(dd, 1H), 0.9(t, 3H).

EXAMPLE 37

Preparation of (S,S)-3-[2-[propyl(1,2,3,4-tetrahydro-5-hydroxy-2-naphthalenyl)amino]ethyl]-1(3H)-isobenzofuranone.

Following the same procedure in Example 36, the lower isomer by TLC (Silica 1:1 pet ether/EtOAc) was isolated and showed characteristic peaks at NMR(300 MHz, CDCl$_3$) $\delta$7.9–6.6(m, 7H) , 5.7 ( dd, 1H) , 0.9 ( t, 3H) .

EXAMPLE 38

Preparation of 1,2,3,4-tetrahydro-7-methoxy-N-(2-phenoxyethyl)-N-propyl-2-naphthalenamine.

Example 29 was repeated using 2-(N-n-propylamino)-7-methoxytetralin in place of (−)-2-(N-n-propylamino)-5-methoxytetralin. The resulting oil was purified by flash chromatography (Silica: 8:2 pet ether/EtOAc) and the product showed characteristic peaks at: NMR (300 MHz, CDCl$_3$) δ7.3–6.6(m, 8H), 4.0(t,2H), 3.75 (S,3H), 0.9(t,3H).

EXAMPLE 39

Preparation of 5,6,7,8-tetrahydro-6-[(2-phenoxylethyl)-propylamino]-3-naphthalenol.

The product of Example 38 was used as the starting material for Example 30. The resulting mixture was subjected to flash chromatography (Silica, 8:2 Pet ether/EtOAc) and the product showed characteristic peaks at: NMR (300 MHz, CDCl$_3$) δ7.2 (m,2H), 6.9(m,3H), 6.55(m,2H), 4.0 (t,2H), 0.9(t,3H).

EXAMPLE 40

Preparation of (−)-1,2,3,4-tetrahydro-5-methoxy-N-[2[(2,5-dimethyl)phenoxy]ethyl]-N-propyl-2-naphthalenamine.

In Example 29, phenoxyacetic acid was replaced with 2,5-dimethylphenoxyacetic acid. The resulting crude was subjected to flash chromatography (Silica: 9:1 Pet ether/EtOAc) and the product showed characteristic peaks at: NMR(300 ,MHz, CDCl$_3$) δ7.1–6.6 (m,6H), 4.0 (t,2H) 3.8 (s,3H), 2.3 (s,3H), 2.15 (s,3H), 0.9(t,3H).

EXAMPLE 41

Preparation of (−)-5,6,7,8-tetrahydro-6-[[2[(2,5-dimethyl)phenoxy]ethyl]propylamino]-1-napthalenol.

The product of Example 40 was used as the starting material in Example 30. The resulting mixture was subjected to flash chromatography (Silica, 8:2 pet ether/EtOAc) and the product showed characteristic peaks at: NMR (300 MHz, CDCl$_3$) δ7.0–6.55 (m, 6H), 4.0(t, 2H), 2.3(s, 3H), 2.15(s, 3H), 0.9(t, 3H).

EXAMPLE 42

Preparation of (+)-1,2,3,4-tetrahydro-5-methoxy-N-[(-2[(2,5-dimethyl)phenoxy]ethyl]-N-propyl-2-naphthalenamine.

In Example 29, phenoxyacetic acid was replaced by 2,5-dimethylphenoxyacetic acid and (−)-2-(N-n-propylamino)-5-methoxytetralin was replaced by (+)-2-(N-n-propylamino)-5-methoxytetralin. The crude mixture was subjected to flash chromatography (Silica: 9:1 pet ether/EtOAc) and the product showed characteristic peaks at: NMR (300 MHz, CDCl$_3$) δ7.1–6.6(m, 6H), 4.0(t, 2H), 3.8(s, 3H), 2.3(s, 3H), 2.15(s, 3H), 0.9(t,3H).

EXAMPLE 43

Preparation of (+)-5,6,7,8-tetrahydro-6-[[2[(2,5-dimethyl)phenoxy]ethyl]propylamino]-1-naphthalenol.

The product of Example 42 was used as the starting material in Example 30. The resulting crude was subjected to flash chromatography (Silica: 8:2 pet ether/EtOAc) and the product showed characteristic peaks at: NMR (300 MHz, CDCl$_3$) δ7.0–6.55 (m, 6H), 4.0(t, 2H), 2.3(s, 3H), 2.5(s, 3H), 0.9(t, 3H).

EXAMPLE 44

Preparation of 1,2,3,4-tetrahydro-5-methoxy-N-[2(3-fluorophenoxy)ethyl]-N-propyl-2-naphthalenamine.

In Example 31, the starting material was replaced with 3-fluorophenoxyacetic acid. The resulting crude was subjected to flash chromatography (Silica: 9:1 Pet ether/EtOAc). The product showed characteristic peaks at: NMR (300 MHz, CDCl$_3$) δ7.2–6.6 (m, 7H) , 4.0 ( t, 2H) , 3.8 ( s, 3H) , 0.9 ( t, 3H) .

EXAMPLE 45

Preparation of 5,6,7,8-tetrahydro-6-[[2(3-fluorophenoxy)ethyl]propylamino]-1-naphthalenol.

In Example 30, the product of Example 44 was used as the starting material. The resulting mixture was subjected to flash chromatography (Silica: 8:2 pet ether-/EtOAc). The product showed characteristic peaks at: NMR (300 MHz, CDCl$_3$) δ7.2–6.5 (m, 7H), 4.0(t, 2H), 0.9(t, 3H).

EXAMPLE 46

Preparation of 6-[[2-(1,3-dihydro-1-isobenzofuranyl)-ethyl]propylamino]-5,6,7,8-tetrahydro-1-naphthalenol.

A racemic mixture of the product of Example 36 (66 mg, 0.180 mmol) was dissolved in THF and added dropwise to a solution of BH$_3$ in THF (2 mL) and the mixture was refluxed overnight. After workup the crude mixture was subjected to flash chromatography (Silica: EtOAc) and the product showed characteristic peaks at: NMR (300 MHz, CDCl$_3$) δ7.3–6.5(m, 7H), 5.4–5.0(m, 3H), 0.9(t, 3H). Anal. calc. for C$_{22}$H$_{29}$NO$_2$·HCl: Theor. C; 71.21; H; 7.79; N, 3.61. Observed: C, 71.16, H, 7.61; N, 3.55.

EXAMPLE 47

Preparation of 1,2,3,4-tetrahydro-5-methoxy-N-[2-(1-naphthalenyloxy)ethyl]-N-propyl-2-naphthalenamine hydrochloride.

In Example 31, the starting material was replaced by (1-naphthoxy)acetic acid. The resulting oil was subjected to flash chromatography (Silica; pet ether) and the product was isolated; characteristic peaks of NMR (300 MHz, CDCl$_3$); δ8.3–6.7(m,10H), 4.2(m, 2H), 3.85(s, 3H), 1.0(t, 3H).

EXAMPLE 48

Preparation of 5,6,7,8-tetrahydro-6-[[2-(1-naphthalenyloxy)ethyl]propylamino]-1-naphthalenol hydrochloride.

The product of Example 47 was used as the starting material in Example 30. The resulting oil was subjected to flash chromatography and the isolated product showed characteristic peaks at: NMR (300 MHz, CDCl$_3$) δ8.3–6.6(m, 10H), 4.2(m, 2H), 0.9(t, 3H).

EXAMPLE 49

Preparation of 1,2,3,4-tetrahydro-5-methoxy-N-(2,2-diphenylethyl)-N-propyl-2-naphthalenamine.

In Example 31, the starting material was replaced by diphenylacetic acid. The purified product showed characteristic peaks at: NMR (300 MHz, CDCl$_3$) δ7.8–6.65 (m, 13H) , 4.1 (t, 1H) , 3.8(s, 3H), 3.2(d, 2H), 0.7(t, 3H).

EXAMPLE 50

Preparation of 6- [(2,2-diphenylethyl)propylamino]-5,6,7,8-tetrahydro-1-naphthalenol.

The product of Example 49 was used as the starting material in Example 30. After purification, the product showed characteristic peaks at: NMR (300 MHz, CDCl$_3$) $\delta$7.8–6.65 (m, 13H), 4.1 (t, 1H), 3.2(d, 2H), 0.7(t,3H). Anal. Calc. for C$_{27}$H$_{31}$NO . HCl: C, 76.84; H, 7.64; N, 3.32. Observed: C, 77.00; H, 7.69; N, 3.21.

EXAMPLE 51

Radioligand Binding Experiments (Dopamine Receptor Affinity Information; pK$_1$ values):

Bovine brains were obtained fresh from a local slaughterhouse. The caudate nuclei were dissected out and homogenized in Buffer A (50 mM Tris; 1 mM Na$_2$-EDTA; 5 mM KCl; 1 mM MgCl$_2$; 2 mM CaCl$_2$; pH 7.4) using a Brinkmann Polytron. The homogenate was centrifuged at 40,000×g for 20 minutes and washed once. The pellet was resuspended in Buffer A, incubated at 37° C. for 15 minutes, then centrifuged. The pellet was washed once more, resuspended to a protein concentration of 5–10 mg/ml in Buffer A and frozen at −70° C. until used.

To test binding of the compounds to dopamine receptors, the following tritiated drugs were used as radioligands for each of the receptors tested: [$^3$H]-Spiperone 21-24 Ci/mmol for D$_2$ receptors and [$^3$H]-SCH23390 75-85 Ci/mmol for D$_1$ receptors. The radioligands were incubated with various concentrations of competing drug and bovine membranes for the following times: 75 minutes at room temperature for D$_2$ receptors, and 15 minutes at 37° C. for D$_1$ receptors. Specific binding was defined using 1 $\mu$M butaclamol (D$_2$) and 1 $\mu$M SCH 23390 (D$_1$). In addition, the D$_2$ assays contained 30 nM ketanserin in order to block the binding of [$^3$H]-spiperone to 5-HT$_2$ receptors.

The assays were terminated by filtration using a 24-port Brandell cell harvester over filters that had been previously soaked in 0.1% polyethyleneimine, and the filters were washed three times by filtration of cold buffer. The filters were then placed in 5 ml scintillation vials to which 4 ml of Beckman Ready-Protein was then added, and each vial was counted for 2 minutes in a Beckman 3801 scintillation counter calibrated for conversion of cpm to dpm. Binding data were analyzed using the Ligand program of Munson and Rodbard (1980). The results are presented as pK$_1$ values in a two-site fitted model.

To test binding to dopamine receptors, the bovine caudate nuclei assay was employed. Bovine brains were obtained fresh from a local slaughterhouse. The caudate nuclei were dissected out and homogenized in Buffer A (50 mM Tris; 1 mM Na$_2$-EDTA; 5 mM KCl; 1 mMMgCl$_2$; 2 mM CaCl$_2$; pH 7.4) using a Brinkman Polytron. The homogenate was centrifuged at 40,000×g for 20 minutes and washed once. The pellet was resuspended in Buffer A, incubated at 37° C. for 15 minutes, then centrifuged. The pellet was washed once more, resuspended to a protein concentration of 5–10 mg/ml in Buffer A and frozen at −70° C. until used.

To test binding of the compounds to $\alpha_2$-adrenergic receptors, the rat cerebral cortex assay was employed. Male Sprague Dawley rats were killed by decapitation and the brains removed. The cerebral cortices were homogenized in 50 mM Tris; 2 mM MgCl$_2$ (pH 7.4), and centrifuged at 40,000×g for 10 minutes. The pellet was washed once, resuspended in Tris/MgCl$_2$ and incubated with 8 units/ml adenosine deaminase at 37° C. for 30 minutes. The homogenate was centrifuged, washed once, resuspended to a protein concentration of 5–10 mg/ml and frozen at −70° C. until used.

The following tritiated drugs were used as radioligands for each of the receptors tested: [$^3$H]-Spiperone 21-24 Ci/mmol for D$_2$ receptors and [$^3$H]-SCH23390 75-85 Ci/mmol for D$_1$ receptors. The radioligands were incubated with various concentrations of competing drug and the appropriate membrane source for periods of time as follows: 75 minutes at room temperature for D$_2$ receptors or 15 minutes at 37° C. for D$_1$receptors. Specific binding was defined using 1 $\mu$M butaclamol (D$_2$) or 1 $\mu$M SCH23390 (D$_1$). In addition, the D$_2$ assays contained 30nM ketaserin in order to block the binding of $^3$H-spiperone to 5HT$_2$ receptors.

The assays were terminated by filtration using a 24-port Brandell cell harvester over filters that had been previously soaked in 0.1% polyethyleneimine, and the filters were washed three times by filtration of cold buffer. The filters were then placed in 5 ml scintillation vials to which 4 ml of Beckman Ready-Protein was then added, and each vial was counted for 2 minutes in a Beckman 3801 scintillation counter calibrated for conversion of cpm to dpm. Binding data were analyzed using the Ligand program of Munson and Rodbard (1980). The results are presented as K$_i$ values if the data were best fitted to a one-site model, or as K$_h$ and K$_1$ values if a two-site model produced the better fit.

Results of the binding tests are summarized in Table I below:

TABLE 1

| | RECEPTOR AFFINITIES | |
|---|---|---|
| Example Number | D$_2$ (pK$_1$) | D$_1$ (pK$_1$) |
| 14 | 6.47 | 5.86 |
| 2 | 6.90 | 4.92 |
| 12 | 7.33 | 5.04 |
| 9 | 7.18 | 5.67 |
| N-0437 | 6.96 | 6.00 |

This table shows high dopamine D$_2$ receptor affinities of compounds chosen from the examples above, with an unexpectedly high degree of selectivity. The compound N-0437, a potent dopamine D$_2$ agonist, is included as a reference compound for comparative purposes.

TABLE 2

| | RECEPTOR AFFINITIES | |
|---|---|---|
| Example Number | D$_2$ (pK$_1$) | D$_1$ (pK$_1$) |
| 30 | 6.77 | 5.06 |
| 48 | 5.94 | 4.87 |
| 46 | 6.77 | 5.14 |
| 32 | 5.58 | 5.38 |
| 34 | 7.10 | 5.89 |
| 36 | 6.85 | 6.56 |
| 37 | 6.91 | 5.91 |
| 39 | 6.09 | 4.91 |
| 45 | 6.50 | 4.98 |

This shows the subject compounds having a high degree of dopamine receptor affinity, particularly the dopamine D$_2$ receptor subtype.

While particular embodiments of the invention have been described, it will be understood, of course, that the invention is not limited thereto since many obvious modifications can be made and it is intended to include within this invention any such modifications as will fall within the scope of the appended claims.

We claim:

1. An optically active compound having the formula

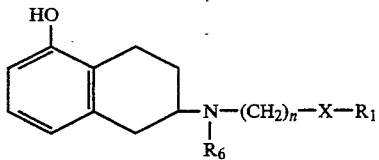

where $R_1$ is selected from the group consisting of

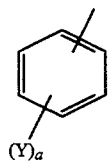

where Y is hydrogen, halogen or $C_1$ to $C_6$ linear or branched alkyl; $R_6$ is $C_1$ to $C_4$ linear or branched alkyl; X is oxygen or sulfur; a is an integer from zero to 3; and n is an integer from 1 to 4.

2. The optically active compound according to claim 1 wherein X is oxygen.

3. The optically active compound according to claim 2 that is (—) -5,6,7,8-tetrahydro-6-[(2-phenoxyethyl)-propyl-amino]-1-napthalenol.

4. The optically active compound according to claim 2 that is (—) -5,6,7,8-tetrahydro-6-[[2(3-fluorophenoxy)ethyl]-propylamino] -1-napthalenol.

5. The optically active compound according to claim 1 wherein X is sulfur.

6. The optically active compound according to claim 5 wherein $R_1$ is

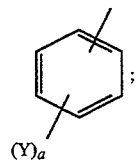

where Y is hydrogen or fluorine; $R_6$ is propyl; and n is 2.

7. The optically active compound according to claim 6 that is 5,6,7,8-tetrahydro-6-[(2-thiophenoxyethyl)-propylamino]-1-naphthalenol.

8. A method comprising administering a dopaminergically-effective amount of a compound represented by the formula

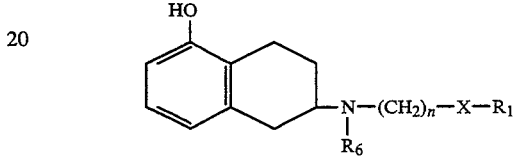

where $R_1$ is selected from the group consisting of

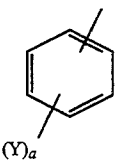

where Y is hydrogen, halogen or $C_1$ to $C_6$ linear or branched alkyl; $R_6$ is $C_1$ to $C_4$ linear or branched alkyl; X is oxygen or sulfur; a is an integer from zero to 3; an n is an integer from 1 to 4 to thereby effect findings to dopamin $D_2$ receptors.

9. The method of claim 8 wherein X is oxygen.

10. The method of claim 9 wherein Y is hydrogen or fluorine; $R_6$ is propyl; and n is 2.

11. The method of claim 10 that is (—) -5,6,7,8-tetrahydro-6-[(2-phenoxyethyl)propyl-amino]-1-napthalenol.

12. The method of claim 10 that is (—) -5,6,7,8-tetrahydro- 6-[[2(3-fluorophenoxy)ethyl]-propylamino]-1-naphthalenol.

13. The method of claim 8 where X is sulfur.

14. The method of claim 13 wherein Y is hydrogen or fluorine; $R_6$ is propyl; and n is 2.

* * * * *